United States Patent
Neumann et al.

(10) Patent No.: US 9,192,631 B2
(45) Date of Patent: Nov. 24, 2015

(54) METHOD FOR OBTAINING HUMAN MICROGLIAL PRECURSOR CELLS FROM PLURIPOTENT STEM CELLS

(75) Inventors: Harald Neumann, Bonn (DE); Kristin Roy, Bonn (DE); Oliver Brüstle, Bonn (DE); Michael Peitz, Bonn (DE)

(73) Assignee: Life & Brain GMBH, Bonn (DE)

( * ) Notice: Subject to any disclaimer, the term of this patent is extended or adjusted under 35 U.S.C. 154(b) by 1011 days.

(21) Appl. No.: 13/266,845

(22) PCT Filed: Apr. 28, 2010

(86) PCT No.: PCT/EP2010/055731
§ 371 (c)(1),
(2), (4) Date: Jan. 18, 2012

(87) PCT Pub. No.: WO2010/125110
PCT Pub. Date: Nov. 4, 2010

(65) Prior Publication Data
US 2012/0107898 A1 May 3, 2012

(30) Foreign Application Priority Data
Apr. 28, 2009 (EP) .................................... 09005880

(51) Int. Cl.
*A61K 35/30* (2015.01)
*C12N 5/0797* (2010.01)
*C12N 5/079* (2010.01)
*A61K 35/12* (2015.01)

(52) U.S. Cl.
CPC .............. *A61K 35/30* (2013.01); *C12N 5/0622* (2013.01); *A61K 35/12* (2013.01); *C12N 2500/25* (2013.01); *C12N 2500/32* (2013.01); *C12N 2500/38* (2013.01); *C12N 2500/44* (2013.01); *C12N 2500/50* (2013.01); *C12N 2501/22* (2013.01); *C12N 2501/2303* (2013.01); *C12N 2501/235* (2013.01); *C12N 2501/58* (2013.01); *C12N 2506/02* (2013.01)

(58) Field of Classification Search
CPC ... A61K 35/12; A61K 35/30; C12N 2500/25; C12N 2500/50; C12N 2506/02; C12N 5/0622; C12N 2501/235; C12N 2501/22; C12N 2501/2303; C12N 2501/58; C12N 2500/38; C12N 2500/32; C12N 2500/44
USPC ............................................... 435/173.9, 366
See application file for complete search history.

(56) References Cited

U.S. PATENT DOCUMENTS

2002/0064877 A1* 5/2002 Kim .............. 435/456

OTHER PUBLICATIONS

Zhang et al. In vitro differentiation of transplantable neural precursors from human embryonic stem cells. Nature Biotechnology. vol. 19, Dec. 2001, p. 1129-1133.*
Ravindran et al. One year survival and significant reversal of motor deficits in parkinsonian rats transplanted with hESC derived dopaminergic neurons. Biochemical and Biophysical Research Communications 373 (2008) 258-264.*
Park et al. Generation of dopaminergic neurons in vitro from human embryonic stem cells treated with neurotrophic factors. Neuroscience Letters 359 (2004) 99-103.*
Giulian et al. Colony-Stimulating Factors as Promoters of Ameboid Microglia. The Journal of Neuroscience, Dec. 1988, B(12): 4707-4717.*
Arsenijevic et al. Insulin-Like Growth Factor-I Is a Differentiation Factor for Postmitotic CNS Stem Cell-Derived Neuronal Precursors: Distinct Actions from Those of Brain-Derived Neurotrophic Factor. The Journal of Neuroscience, Mar. 15, 1998, 18(6):2118-2128.*
Hsieh et al. IGF-I instructs multipotent adult neural progenitor cells to become oligodendrocytes. The Journal of Cell Biology, vol. 164, No. 1, Jan. 5, 2004 111-122.*
Cosenza-Nashat et al. CD45 Isoform Expression in Microglia and Inflammatory Cells in HIV-1 Encephalitis. Brain Pathol 2006;16:256-265.*
Merrill. Macroglia: neural cells responsive to lymphokines and growth factors. Immunology Today. vol. 8, No. 5, 1987. p. 146.*
Banati, Riachard B., "Neuropathological Imaging: in vivo detection of glial activation as a measure of disease and adaptive change in the brain", British Medical Bulletin 2003; 65: 121-131.
Biber, Knut, et al., "Neuronal 'On' and 'Off' signals control microglia", Trends in Neurosciences, vol. 30 No. 11, 596-602.
Blasi, E., et al., "Immortalization of murine microglial cells by a v-raf/v-myc carrying retrovirus", Journal of Neuroimmunology, 27 (1990): 229-237.
Bocchini, V., et al., "An Immortalized Cell Line Expresses Properties of Activated Microglial Cells", Journal of Neuroscience Research 31 (1992): 616-621.

(Continued)

*Primary Examiner* — Taeyoon Kim
(74) *Attorney, Agent, or Firm* — Ohlandt, Greeley, Ruggiero & Perle, L.L.P.

(57) ABSTRACT

A method for obtaining human microglial precursor cells, comprising: (a) providing a cell population comprising neural precursor cells, wherein the cell population is obtainable from embryoid bodies differentiated from human pluripotent stem cells; (b) differentiating the cell population comprising neural precursor cells into microglial precursor cells by culturing in medium comprising a growth factor selected from the group consisting of insulin and insulin-like growth factors; (c) expanding and enriching microglial precursor cells in medium comprising a growth factor selected from the group consisting of insulin and insulin-like growth factors and 10 to 150 ng/ml GM-CSF; and (d) isolating microglial precursor cells comprising CD45-positive cells.

13 Claims, 3 Drawing Sheets
(2 of 3 Drawing Sheet(s) Filed in Color)

(56) References Cited

OTHER PUBLICATIONS

Carter, Sally L., et al., "Induction of the Genes for Cxcl9 and Cxcl10 is Dependent on IFN-g but Shows Differential Cellular Expression in Experimental Autoimmune Encephalomyelitis and by Astrocytes and Microglia In Vitro", GLIA 55 (2007): 1728-39.

Chan, W.Y., et al., "The origin and cell lineage of microglia—New concepts", Brain Research Reviews, 53 (2007): 344-354.

Choi, K. D., et al., "Hematopoietic and Endothelial Differentiation of Human Induced Pluripotent Stem Cells", Stem Cells 2009;27:559-567.

Dainiak, Maria B., et al., "Methods in Cell Separations", Adv Biochem Engin/Biotechnol (2007) 106: 1-18.

Durkin, M.E., et al., Tissue-specific expression of the human laminin alpha5-chain, and mapping of the gene to human chromosome 20q13.2-13.3 and to distal mouse chromosome 2 near the locus for the ragged (Ra) mutation. FEBS Lett. 411 (2-3),: 296-300.

Ford, Andrew L., et al., "Normal Adult Ramified Microglia Separated from Other Central Nervous System Macrophages by Flow Cytometric Sorting Phenotypic Differences Defined and Direct Ex Vivo Antigen Presentation to Myelin Basic Protein-Reactive CD4+ T Cells Compared", The Journal of Immunology, 1995, 154: 4309-4321.

Giulian, Dana, et al., "Characterization of ameboid microglia isolated from developing mammalian brain", The Journal of Neuroscience, Aug. 1986, 6(8): 2163-2178.

Gourmala, Nouciba G., et al., "Differential and time-dependent expression of monocyte chemoattractant protein-1 mRNA by astrocytes and macrophages in rat brain: effects of ischemia and peripheral lipopolysaccharide administration", Journal of Neuroimmunology 74 (1997): 35-44.

Hanisch, U.K, et al., "Microglia: active sensor and versatile effector cells in the normal and pathologic brain", Nature Neuroscience, vol. 10, No. 11, Nov. 2007: 1387-1394.

Horvath, R. J., et al., "Differential migration, LPS-induced cytokine, chemokine, and NO expression in immortalized BV-2 and HAPI cell lines and primary microglial cultures", Journal of Neurochemistry (2008), 107: 557-569.

Hughes, P.M., et al., "Expression of Fractalkine (CX3CL1) and Its Receptor, CX3CR1, During Acute and Chronic Inflammation in the Rodent CNS", GLIA (2002) 37(4):314-327.

Iwasaki, Hiromi, et al., "Distinctive and indispensable roles of PU.1 in maintenance of hematopoietic stem cells and their differentiation", Blood, 2005 106: 1590-1600.

Jung, Steffen, et al., "Analysis of Fractalkine Receptor CX3CR1 Function by Targeted Deletion and Green Fluorescent Protein Reporter Gene Insertion", Molecular and Cellular Biology, 2000, vol. 20 No. 11: 4106-4114.

Kamihira, Masamichi, et al., "Development of Separation Technique for Stem Cells", Adv Biochem Engin/Biotechnol (2007) 106: 173-193.

Klimanskaya, Irina, et al., "Human embryonic stem cell lines derived from single blastomeres", Nature, vol. 444, Nov. 23, 2006: 481-85.

Kurokawa, T., et al., "Cloning and expression of cDNA encoding human basic fibroblast growth factor", FEBS Lett., Mar. 1987, vol. 213, No. 1: 189-194.

LaFortune, Louise, et al., "Expression of Tumor Necrosis Factor (TNF) and Interleukin 6 (IL-6) mRNA in Adult Human Astrocytes: Comparison with Adult Microglia and Fetal Astrocytes", Journal of Neuropathology and Experimental Neurology, vol. 55, No. 5: 515-521.

Lee, Frank, et al., "Isolation of cDNA for a human granulocyte-macrophage colony-stimulating factor by functional expression in mammalian cells", Proc. Nati. Acad. Sci. USA, vol. 82, Jul. 1985: 4360-4364.

Liu, W., et al., "Macrophage Colony-Stimulating Factor Mediates Astrocyte-Induced Microglial Ramification in Human Fetal Central Nervous System Culture", American Journal of Pathology, vol. 145, No. 1, Jul. 1994: 48-53.

Napoli,, I., et al., "Microglial Precursors Derived from Mouse Embryonic Stem Cells", GLIA 57 (2009):1660-1671.

Nimmerjahn, Axel, et al., "Resting Microglial Cells Are Highly Dynamic Surveillants of Brain Parenchyma in Vivo", Science 308, (2005):1314-1318.

Nishikawa, Shin-ichi, et al., "The promise of human induced pluripotent stem cells for research and therapy", Nature Reviews molecular cell biology, vol. 9, Sep. 2008: 725-9.

Park, I.H., et al., "Generation of human-induced pluripotent stem cells", Nature Protocols, vol. 3 No. 7 (2008): 1180-1186.

Pevny, Larysa H., et al., "A role for SOX1 in neural determination", Development 125 (1998): 1967-1978.

Ransohoff, R.M., et al., "Microglial Physiology: Unique Stimuli, Specialized Responses", Annu Rev Immunol. 2009 27: 119-45.

Rüegg, Curzio, et al., "Role of Integrin a4β7/a4βP in Lymphocyte Adherence to Fibronectin and VCAM4 and in Homotypic Cell Clustering", The Journal of Cell Biology, vol. 117, No. 1, Apr. 1992: 179-189.

Schmid, Christoph D., et al., "Heterogeneous expression of the triggering receptor expressed on myeloid cells-2 on adult murine microglia", Journal of Neurochemistry, 2002, 83: 1309-1320.

Takahashi, Kazuya, et al., "Clearance of apoptotic neurons without inflammation by microglial triggering receptor expressed on myeloid cells-2", vol. 201, No. 4, Feb. 21, 2005: 647-657.

Takahashi, M., et al., "Amino-Terminal Region of Human Macrophage Colony-Stimulating Factor (M-CSF) Is Sufficient for Its -I-N Vitro Biological Activity: Molecular Cloning and Expression of Carboxyl-Terminal Deletion Mutants of Human M-CSF", Biochemical and Biophysical Research Communications, vol. 161, No. 2, 1989, Jun. 15, 1989: 892-901.

Takashima, Y., et al., "Neuroepithelial Cells Supply an Initial Transient Wave of MSC Differentiation", Cell 129, Jun. 29, 2007: 1377-1388.

Tsuchiya, T., et al., "Characterization of microglia induced from mouse embryonic stem cells and their migration into the brain parenchymaB", Journal of Neuroimmunology, 160 (2005): 210-218.

Vaughan, D.W., et al., "Neuroglial cells in the cerebral cortex of rats from young adulthood to old age: an electron microscope study", 3 (1974): 405-429.

Vuolteenaho, R., et al., "Structure of the Human Laminin BI Chain Gene", The Journal of Biological Chemistry, vol. 265, No. 26. Issue of Sep. 15, 1990: 15611-15616.

Wong, G.G., et al., "Human GM-CSF: Molecular Cloning of the Complementary DNA and Purification of the Natural and Recombinant Proteins", Science, vol. 228: 810-815.

Yang, Y.C., et al., "Human IL-3 (Multi-CSF): Identification by Expression Cloning of a Novel Hematopoietic Growth Factor Related to Murine IL-3", Cell, vol. 47, Oct. 10, 1988: 3-10.

Zhang, J., et al., "Functional Cardiomyocytes Derived From Human Induced Pluripotent Stem Cells", Circulation Research 2009, 104: e30-e41.

Zhou, W., et al., "Adenoviral Gene Delivery Can Reprogram Human Fibroblasts to Induced Pluripotent Stem Cells", Stem Cells 2009; 27: 2667-2674.

Napoli, I., "Establishment of Embryonic Stem Cell Derived Microglial Precursors and Application in an Animal Model of Alzheimer's Disease", PhD thesis, 2008, at the Faculty of Mathematics and Natural Sciences of the Rheinischen Friedrich-Wilhelms University of Bonn.

Park, I.H., et al., "Human iPS Cell Derivation/Reprogramming", Current Protocols in Stem Cell Biology, Chapter 4: 4A.1.1-4A.1.8.

Block, M.L. and Hong, J.S. (2007). Chronic microglial activation and progressive dopaminergic neurotoxicity. Biochem Soc Trans 35, 1127-1132.

Schmitz, S. (2009). Der Experimentator: Zellkultur. Spektrum Akademischer Verlag, 3 Aufl.

* cited by examiner

METHOD FOR OBTAINING HUMAN MICROGLIAL PRECURSOR CELLS FROM PLURIPOTENT STEM CELLS

BACKGROUND

1. Field of the Disclosure

The present disclosure relates to a method for obtaining human microglial precursor cells, comprising: (a) providing a cell population comprising neural precursor cells, wherein the cell population is obtainable from embryoid bodies differentiated from human pluripotent stem cells; (b) differentiating the cell population comprising neural precursor cells into microglial precursor cells by culturing in medium comprising a growth factor selected from the group consisting of insulin and insulin-like growth factors; (c) expanding and enriching microglial precursor cells in medium comprising a growth factor selected from the group consisting of insulin and insulin-like growth factors and 10 to 150 ng/ml GM-CSF; and (d) isolating microglial precursor cells comprising CD45-positive cells.

2. Discussion of the Background Art

In this specification, a number of documents including patent applications and manufacturer's manuals is cited. The disclosure of these documents, while not considered relevant for the patentability of this disclosure, is herewith incorporated by reference in its entirety. More specifically, all referenced documents are incorporated by reference to the same extent as if each individual document was specifically and individually indicated to be incorporated by reference.

Microglia are the resident immune cells of the central nervous system (CNS) and constitute about 10 to 20% of all glial cells in the adult CNS (Banati, 2003; Vaughan and Peters, 1974). The origin of microglia is still unclear. It was suggested that microglia appear in two waves, firstly in the neuroepithelium with unknown origin (Chan et al., 2007) and secondly in the brain during fetal development derived from the hematopoietic system and of mesodermal origin (Block and Hong, 2007; Chan et al., 2007).

Microglia respond to damage signals coming from injured tissue by undergoing activation of immune defence programs and proliferation (Ransohoff and Perry, 2009). Thus, microglia are responsible for the first line of the innate immune response in the CNS (Biber et al., 2007; Block et al., 2007; Hanisch and Kettenmann, 2007). Microglia are believed to remain in a resting stage under healthy physiological conditions. This stage is characterized by a ramified morphology and low expression of immunological molecules. In order to perform their surveillance function, microglia are highly dynamic during the resting stage and screen their environment. It is estimated that microglia can scan the entire brain parenchyma every few hours (Hanisch and Kettenmann, 2007; Nimmerjahn et al., 2005).

Under pathological conditions like injury or inflammation microglia become activated immune cells that show an amoeboid morphology, migrate to and within the lesion site, can clear apoptotic cells by phagocytosis and release a wide range of soluble factors that include neurotrophins and immunomodulatory factors (Biber et al., 2007; Block et al., 2007; Hanisch and Kettenmann, 2007). However, in some neurodegenerative diseases like Alzheimer's disease and multiple sclerosis, microglia become over-activated and have detrimental effects on neurons by releasing cytotoxic factors like nitric oxide and tumor necrosis factor-alpha (Block et al., 2007).

Microglial function is often studied using primary microglial cells, which are isolated and enriched from mixed glial cultures derived from the brains of postnatal mice or rats. A restricted number of microglial cells are obtained by a shaking procedure from mixed glial culture flasks (Giulian and Baker, 1986). Optionally, a purified population of microglial cells can be obtained using density gradients and flow cytometry sorting (Ford et al., 1995). Human primary microglia have also been obtained in very limited numbers from patients undergoing neurosurgery or from autopsy brains obtained after a short post mortem interval (Lafortune et al., 1996)

However, the obtained number of primary microglia is very limited in rodents and humans, which complicates classical biochemistry studies, systematic screening tests, or cell therapy approaches. In addition to primary cells, a murine microglial cell line (BV2) was developed by oncogenic transformation of primary microglia (Blasi et al., 1990; Bocchini et al., 1992). Furthermore, an immortalised human microglial cell line (HMO6) was developed through retroviral transduction of human embryonic telencephalon tissue with v-myc (U.S. Pat. No. 6,780,641). However, a drawback of all these cell lines is that they showed altered cytokine profile and changes in their migratory capacity (Horvath et al., 2008).

Recently, differentiation of microglia-like cells from mouse embryonic stem (ES) cells was described using a five-step protocol following neuronal differentiation (Tsuchiya et al., 2005). Tsuchiya et al. succeeded in differentiating Mac1+ cells into macrophages as well as into microglia and in isolating microglial cells that were positively stained for Iba1 and CD45, by a density gradient method. The isolated cells showed morphological characteristics of primary microglia and migrate from the bloodstream to brain parenchyma in mice. However, these cells were not described to survive and proliferate in culture (Tsuchiya et al., 2005). Recently, several microglial precursor cell lines were generated from murine ES cells (Napoli et al., 2009). The murine ES cell-derived microglial precursor (ESdM) lines were propagated in culture and expanded to high cell numbers. ESdM were indistinguishable by their cell surface receptors from primary microglia and showed migratory and phagocytic capacity comparable to primary microglia. After intracerebral transplantation in postnatal mice, they engrafted as microglial cells into the brain tissue.

However, despite the above described advances in the establishment of microglia precursor cell cultures, there is still the need to provide methods for the preparation of high quality human microglial precursor cells that can be obtained in large quantities.

SUMMARY

Accordingly, the present disclosure relates to a method for obtaining human microglial precursor cells, comprising: (a) providing a cell population comprising neural precursor cells, wherein the cell population is obtainable from embryoid bodies differentiated from human pluripotent stem cells; (b) differentiating the cell population comprising neural precursor cells into microglial precursor cells by culturing in medium comprising a growth factor selected from the group consisting of insulin and insulin-like growth factors; (c) expanding and enriching microglial precursor cells in medium comprising a growth factor selected from the group consisting of insulin and insulin-like growth factors and comprising 10 to 150 ng/ml GM-CSF; and (d) isolating microglial precursor cells comprising CD45-positive cells.

In accordance with the present disclosure, the term "microglial precursor cells" relates to a population of cells comprising partially differentiated cells, derived from myeloid precursor cells and capable of further differentiating into microglial cells. Myeloid precursor cells are characterized by the expression of the transcription factor PU.1 (Iwasaki et al. (2005). Microglia are further characterized by a ramified morphology with processes interdigitating with other glial cells and neurons and in surveying their local environment (Ransohoff and Perry, 2009). Furthermore, upon transplantation of microglial precursor cells into tissues comprising neurons and astrocytes, they integrate into these tissues as microglia (Tsuchiya et al., 2005; Napoli, 2008). In addition, upon contact of microglial precursors with neurons and/or astrocytes or addition of growth factors such as macrophage colony-stimulating factor, they can transform into microglia (Liu et al., 1994). The population of "microglial precursor cells" may comprise cells at different stages of differentiation between myeloid precursor cells and microglia. Thus, also fully differentiated microglial cells may be comprised in the population of microglial precursor cells. Non-differentiated stem cells as well as neural or mesenchymal stem cells are not comprised in the term "microglial precursor cells".

Preferably, the microglial precursor cells are a population comprising at least 70% of cells expressing the markers of CD45, CD11b, CD11c, CD14, CD16, integrin-alpha4, inegrin-beta1, CX3CR1 and TREM2 and being inducible to express TNF-alpha, interleukin-1 beta, nitric oxide synthase-2, CCL2, CXCL9 and/or CXCL10 (Napoli, 2008). More preferably, at least 80%, such as at least 90%, at least 95% and most preferably 100% of the cells express the markers CD45, CD11b, CD11c, CD14, CD16, integrin-alpha4, integrin-beta1, CX3CR1 and TREM2 and being inducible to express TNF-alpha, interleukin-1 beta, nitric oxide synthase-2, CCL2, CXCL9 and/or CXCL10.

The term "neural precursor cells" refers to cells of neuroectodermal origin that are capable of differentiating into various neural cell types. Such neural cell types include for example neurons, astrocytes and oligodendrocytes. Neuroectodermal cells are characterized by the expression of SOX1, an HMG box transcription factor (Pevny et al., 1998).

The "cell population comprising neural precursor cells" preferably is a population comprising at least 70% of neural precursor cells, more preferably at least 80%, such as at least 90%, at least 95% and most preferably 100% neural precursor cells. The cell population may further comprise a small number (e.g. 5%, 10%, 20% or 30%) of stem cells showing mesenchymal properties, and which are derived from SOX1-positive neuroectodermal cells (Takashima et al., 2007).

The term "embryoid bodies" as used herein refers to aggregates of cells derived from pluripotent stem cells. Embryoid bodies (embryoid body) are generally comprised of a large variety of differentiated cell types. Cell aggregation is for example imposed by hanging drop or other methods that prevent cells from adhering to a surface, thus allowing the embryoid bodies to form their typical colony growth. Upon aggregation, differentiation is typically initiated and the cells begin to a limited extent to recapitulate embryonic development.

The term "pluripotent stem cells", in accordance with the present disclosure, relates to a cell type having the capacity for self-renewal, an ability to go through numerous cycles of cell division while maintaining the undifferentiated state, and the potential of differentiation, i.e. the capacity to differentiate into specialized cell types. Pluripotent stem cells are the descendants of totipotent cells and can differentiate into nearly all cells, i.e. cells derived from any of the three primary germ layers: ectoderm, endoderm, and mesoderm. The term pluripotent stem cells also encompasses stem cells derived from the inner cell mass of an early stage embryo known as a blastocyst. Recent advances in embryonic stem cell research have led to the possibility of creating new embryonic stem cell lines without destroying embryos, for example by using a single-cell biopsy similar to that used in preimplantation genetic diagnosis (PGD), which does not interfere with the embryo's developmental potential (Klimanskaya et al., 2006). Furthermore, a large number of established embryonic stem cell lines are available in the art (according to the U.S. National Institutes of Health, 21 lines are currently available for distribution to researchers), thus making it possible to work with embryonic stem cells without the necessity to destroy an embryo.

In a preferred embodiment, the pluripotent stem cells are not human embryonic stem cells.

In an alternative preferred embodiment, the pluripotent stem cells are induced pluripotent stem cells. "Induced pluripotent stem (iPS) cells", in accordance with the present disclosure, are pluripotent stem cells derived from a non-pluripotent cell, typically an adult somatic cell, by inducing a "forced" expression of certain genes. Induced pluripotent stem cells are identical to natural pluripotent stem cells, such as e.g. embryonic stem cells, in many respects including for example the expression of certain stem cell genes and proteins, chromatin methylation patterns, doubling time, embryoid body formation, teratoma formation, viable chimera formation, and potency and differentiability. Induced pluripotent stem cells are an important advancement in stem cell research, as they allow researchers to obtain pluripotent stem cells without the use of embryos (Nishikawa et al., 2008). The induced pluripotent stem cells may be obtained from any adult somatic cell, preferably from fibroblasts, such as for example from skin tissue biopsies.

Methods for the generation of human induced pluripotent stem cells are well known to the skilled person. For example, induced pluripotent stem cells can be generated from human skin tissue biopsies (Park and Daley, 2009; Park et al., 2008). Fibroblasts are grown in MEM-medium containing chemically defined and recombinant serum components. For reprogramming, the human fibroblasts are retrovirally transduced with OCT4, SOX2, c-MYC and NANOG genes. For this, genes are cloned into a retroviral vector and transgene-expressing viral particles are produced in the HEK293FT cell line. Human skin fibroblasts are co-transduced with all four vectors. The obtained iPS cells are cultured according to protocols established for human embryonic stem cells in DMEM-medium containing serum replacement factors and recombinant growth factors. The iPS cells are analyzed for normal morphology and normal karyotype and are studied by fingerprinting analysis and immunostaining for OCT3/4, NANOG, SSEA-3, SSEA-4, Tra-1-60 and Tra-1-81. Gene transcripts for OCT4, SOX2, NANOG, KLF4, c-MYC, REX1, GDF3 and hTERT are analyzed by real-time RT-PCR. Furthermore, multilineage differentiation of iPS cells is confirmed by embryoid body, teratoma formation and differentiation into adult cell types (Choi et al., 2009; Zhang et al., 2009). As another example, human iPS cells can also be obtained from embryonic fibroblasts without viral integration using adenoviral vectors expressing c-Myc, Klf4, Oct4, and Sox2 (Zhou and Freed, 2009).

The term "a cell population obtainable from embryoid bodies differentiated from human pluripotent stem cells" as used in accordance with the present disclosure refers to a cell population comprising neural precursor cells having the same characteristics as a cell population obtained after inducing human pluripotent stem cells to form embryoid bodies and culture them under conditions that allow the expansion of nestin-positive cells.

The "growth factor" as used herein refers to a factor capable of stimulating cellular growth, proliferation and differentiation. The term "a growth factor selected from the group consisting of insulin and insulin-like growth factors" refers to a growth factor selected from insulin and polypeptides with high sequence similarity to insulin, in particular insulin-like growth factor 1 (IGF-1) and insulin-like growth factor 2 (IGF-2).

The growth factor selected from the group consisting of insulin and insulin-like growth factors may be comprised in the medium in amounts of between 5 to 500 μg/ml, preferably between 10 to 350 μg/ml, more preferably between 15 to 200 μg/ml, such as for example 18 to 100 μg/ml, such as for example 22 to 50 μg/ml and most preferably at about 25 μg/ml.

Preferably, the differentiation of the cell population comprising neural precursor cells into microglial precursor cells in step (b) is carried out in the absence of feeder cells.

Appropriate culture media are known in the art and comprise, for example, media containing L-glutamine, D-glucose, insulin, transferrin, progesterone, putrescine and/or sodium-selenite. For example, a preferred medium for differentiating the cell population comprising neural precursor cells into microglial precursor cells in step (b) is N2-medium, i.e. a Dulbecco's Modified Eagle Medium: Nutrient Mixture F-12 (DMEM/F12)-based medium comprising 0.48 mM L-glutamine, 5.3 μg/ml D-glucose, 25 μg/ml insulin, 100 μg/ml transferrin, 6.3 ng/ml progesterone, 16.11 μg/ml putrescine and 5.2 ng/ml sodium-selenite. In accordance with the present disclosure, the cell culture medium employed in step (b) lacks FGF2, which, together with the absence of self-renewal signals usually produced by feeder layers, leads to spontaneous differentiation of the cells into embryoid bodies.

A preferred medium for expanding and enriching microglial precursor cells in step (c) is also N2-medium as defined above, further comprising 10 to 150 ng/ml GM-CSF as characterised in step (c).

The term "GM-CSF" as used herein refers to granulocyte-macrophage colony-stimulating factor, a cytokine that functions as a white blood cell growth factor (Wong et al., 1985; Lee et al., 1985). GM-CSF stimulates stem cells to produce granulocytes (neutrophils, eosinophils, and basophils) and monocytes and is secreted by macrophages, T cells, mast cells, endothelial cells and fibroblasts. GM-CSF may be comprised in the medium in amounts of 10 to 150 ng/ml, preferably between 30 to 130 ng/ml, more preferably between 50 and 120 ng/ml, such as for example 70 to 110 ng/ml and most preferably at about 100 ng/ml.

The term "expanding", in accordance with the present disclosure, refers to a multiplication of cells, thus resulting in an increase in the total number of microglial precursor cells. Preferably, cells are expanded to at least twice their original number, more preferably to at least 10 times their original number, such as for example at least 100 times, such as at least 1,000 times their original number and most preferably to at least 10,000 times, such as at least 100,000 times their original number.

Expansion of microglial precursor cells may be achieved by known methods, e.g. by culturing the cells under appropriate conditions to high density and subsequent splitting (or passaging) of the cells, wherein the cells are re-plated at a diluted concentration into an increased number of culture dishes or onto solid supports. With increasing passage number, the amount of cells obtained therefore increases due to cell division.

In accordance with the present disclosure, the term "enriching" refers to a selective accumulation of microglial precursor cells, thus resulting in an increase of the number of microglial precursor cells as compared to the number of cells that are not microglial precursor cells. Preferably, cells are enriched such that at least 70% of the cell population are microglial precursor cells. More preferably, at least 80%, such as at least 90%, at least 95%, at least 98%, such as at least 99% and most preferably 100% of the cell population are microglial precursor cells.

Enrichment of microglial precursor cells may be achieved by any method known in the art. For example, microglial precursor cells appear as rounded, bright shining cells that can be distinguished from neurons by their cellular body. Therefore, microglial precursor cells can be identified by their morphology and can be mechanically isolated and transferred to a solid support, such as for example a different cell culture dish or flask. Mechanical isolation relates to the manual selection and isolation of cells, preferably under a microscope and may be performed by methods known in the art, such as for example aspiration of the cells into the tip of pipette or detaching of the cells using a cell scraper or density gradient centrifugation (Kamihira and Kumar, 2007).

As an alternative exemplary method of enriching microglial precursor cells, the cells may be maintained in culture as defined in step (c) for a prolonged period of time, such as for example two or more weeks until the microglial precursor cells have overgrown the remaining cell types, which do not survive under these conditions. During this prolonged culture period, the medium is preferably replaced with fresh medium. Most preferably, the medium is replaced ever second day.

Further methods of enrichment include, without being limiting, cell sorting approaches such as magnetic activated cell sorting (MACS) or flow cytometry activated cell sorting (FACS), panning approaches using immobilised antibodies or the use of density gradients. All these methods are known to the person skilled in the art and have been described, for example in Dainiak et al., 2007.

Methods of isolating microglial precursor cells comprising CD45-positive cells are well-known in the art and comprise, without being limiting, cell sorting approaches such as for example the above mentioned methods of magnetic activated cell sorting (MACS), flow cytometry activated cell sorting (FACS), panning approaches using immobilised antibodies, high-throughput fluorescence microscopy or density gradient approaches. Any surface protein expressed, preferably selectively expressed (i.e. not expressed or not expressed to a significant amount on other cell types present in the culture), on microglial precursor cells may be employed for this isolation, as long as the cells thereby obtained comprise CD45-positive cells. Such surface proteins are described further below. Preferably, the isolation is carried out based on the surface protein CD45. In accordance with the present disclosure, the term "microglial precursor cells comprising CD45-positive cells" refers to a cell population comprising at least 70% of cells expressing the marker CD45. More preferably, at least 80%, such as at least 90%, at least 95%, at least 98%, such as at least 99% and most preferably 100% of the cells express the marker CD45.

"CD45", as used herein, refers to "cluster of differentiation 45" and is a membrane tyrosine phosphatase that is used as a marker to distinguish cells of the hematopoietic lineage from the endothelial lineage. CD45 is uniformly distributed in the plasma membrane and constitutes up to 10% of the molecules on the surface of expressing cells (Ford et al., 1995).

In accordance with the present disclosure, it was surprisingly found that human pluripotent stem cells can be differentiated into microglial precursor cells in cell culture.

So far, methods employing human microglial precursor cells are severely limited by the fact that the only available human microglial precursor cell lines are either primary cell lines or immortalised human microglial cell lines, which are obtained by retroviral transduction of cells. Both of these cell lines have drawbacks. Primary cell lines can only be obtained in limited numbers, which often is insufficient for classical biochemistry studies, systematic screening tests, or cell therapy approaches. Immortalised human microglial cell lines, on the other hand, have the drawback that due to the transformation they potentially have an altered cytokine profile and therefore show changes in their behaviour such as their migratory capacity.

The present disclosure now provides a method of preparing human microglial precursor cells that are of high quality and can be obtained in large quantities. The method thus provides the advantage of providing human microglial precursor cells as a cell line that can be amplified and maintained for a prolonged period of time, thus providing a sufficiently high number of cells for carrying out research, such as for example research and validation studies of pharmaceutical compositions for use in the central nervous system or toxicity studies such as for example for studying the inflammatory potential of substances, for example nanoparticles. Also, the microglial precursor cells obtained by the method of the present disclosure may be used in novel methods of cell therapy, such as in the treatment of neuro-degenerative, neuro-inflammatory or neuro-oncological diseases.

In a preferred embodiment of the method of the disclosure, the cell population comprising neural precursor cells in step (a) is obtained by: (i) growing human pluripotent stem cells in suspension culture until embryoid bodies have formed; (ii) transferring the embryoid bodies onto a solid support under conditions suitable to allow attachment of the embryoid bodies and culturing the embryoid bodies until the embryoid bodies have attached to the solid support; (iii) changing the medium to neural precursor selection medium comprising (1) a growth factor selected from the group consisting of insulin and insulin-like growth factors, (2) 5 to 100 ng/ml FGF2 and (3) 2.5 to 25 μg/ml fibronectin or 5 to 50 ng/ml laminin and culturing the embryoid bodies for at least 10 days; and (iv) expanding nestin-positive cells in medium comprising a growth factor selected from the group consisting of insulin and insulin-like growth factors and comprising 5 to 100 ng/ml FGF2 and 5 to 50 ng/ml laminin for at least 7 days.

The term "suspension culture" as used herein refers to the culture of cells such that the cells do not adhere to the solid support or the culture vessel. To transfer cells into a suspension culture, they are for example removed from the culture dish by a cell scraper and transferred to sterile dishes (e.g. bacterial dishes) containing culture medium, which do not allow adhesion of the cells to the surface of the dish. Thus, the cells are cultured in suspension without adherence to a matrix or the bottom of the dish.

The term "solid support", in accordance with the present disclosure, refers to a surface enabling the adherence of cells thereto. Said surface may be, for example, the wall or bottom of a culture vessel, a plastic or glass slide such as for example a microscope slide or (a) bead(s) offering a surface for adherence.

"Conditions suitable to allow attachment", as referred to herein, are well known to the skilled person and have been described, for example, in Schmitz, 2009. Preferably, said conditions are achieved by coating the solid support with an agent that enhances attachment of cells to the solid support. Such coating agents as well as methods of using them are also well known in the art and include, without being limiting, poly-L-lysin, gelatine, poly-L-ornithin, collagen, tenascin, perlecan, phosphocan, brevican, neurocan, thrombospondin, fibronectin and laminin, as for example described in the examples below.

The terms "FGF2", "fibronectin" and "laminin" are used according to the definitions provided in the art. Thus, FGF2 refers to the basic fibroblast growth factor, a member of the fibroblast growth factor family, also referred to as bFGF or FGF-β in the art (Kurokawa et al., 1987).

Fibronectin refers to a high-molecular weight (~440 kDa) extracellular matrix glycoprotein that binds to integrins but also to other extracellular matrix components such as collagen, fibrin and heparan sulfate proteoglycans (e.g. syndecans) (Ruegg et al., 1992).

Laminin refers to a family of glycoproteins that are an integral part of the structural scaffolding in almost every tissue of an organism. They are secreted and incorporated into cell-associated extracellular matrices. Fibronectin and laminin promote attachment, spreading, and proliferation of cells in cell culture (Vuolteenaho et al., 1990; Durkin et al., 1997).

FGF2 may be comprised in the medium in amounts of between 5 to 100 ng/ml, preferably between 8 to 75 ng/ml, more preferably between 12 and 50 ng/ml, such as for example 15 to 40 ng/ml, such as for example 17 to 30 ng/ml and most preferably at about 20 ng/ml.

Fibronectin may be comprised in the medium in amounts of between 2.5 to 25 μg/ml, preferably between 3 to 20 μg/ml, more preferably between 3.5 to 15 μg/ml, such as for example 4 to 10 μg/ml, such as for example 4.5 to 8 μg/ml and most preferably at about 5 μg/ml.

Laminin may be comprised in the medium in amounts of between 5 to 50 ng/ml, preferably between 8 to 40 ng/ml, more preferably between 12 and 30 ng/ml, such as for example 15 to 25 ng/ml, such as for example 17 to 22 ng/ml and most preferably at about 20 ng/ml.

The term "nestin-positive cells", as used herein, refers to cells expressing the marker nestin, which is a type VI intermediate filament protein.

In addition to the media defined above, another exemplary medium to be used in the method of the present disclosure, in particular in step (iii) is B27-medium, i.e. a Dulbecco's Modified Eagle Medium: Nutrient Mixture F-12 (DMEM/F12)-based medium comprising 0.2 mM L-glutamine, 15.6 μg/ml D-glucose, 25 μg/ml insulin, 30 nM sodium-selenite and 50 μg/ml transferrin.

In another preferred embodiment of the method of the disclosure, the cells are further cultured after step (d) for at least 2 passages in medium comprising 10 to 150 ng/ml GM-CSF and a growth factor selected from the group consisting of insulin and insulin-like growth factors on a solid support under conditions suitable to allow attachment of the cells.

In a more preferred embodiment, the microglial precursor cells are, following the culturing for 2 passages, maintained in medium comprising a growth factor selected from the group consisting of insulin and insulin-like growth factors. In an alternative embodiment, the microglial precursor cells obtained according to the method of the disclosure are maintained in medium comprising a growth factor selected from the group consisting of insulin and insulin-like growth factors, without the above described further culturing step for at least 2 passages in medium comprising 10 to 150 ng/ml GM-CSF and a growth factor selected from the group consisting of insulin and insulin-like growth factors on a solid support under conditions suitable to allow attachment of the cells.

It was found in accordance with the present disclosure, that the cells obtained with the method of the disclosure can proliferate without addition of any of the growth factors GM-CSF, M-CSF or IL-3 to medium. Furthermore, the microglial precursor cells are capable of attaching to solid supports without requiring the coating with any coating agents, such as poly-L-lysin. However, it is preferred that the initial at least two passages are carried out in the presence of said factors in order to increase attachment and proliferation rate.

In a further preferred embodiment of the method of the disclosure, enriching in step (c) comprises transferring microglial precursor cells onto a solid support under conditions suitable to allow attachment of the cells.

As outlined above, the microglial precursor cells may be enriched using various methods known in the art. In accordance with this preferred embodiment, the cells are actively enriched, for example by the methods referred to above such as mechanical isolation based on morphology, cell sorting approaches, panning methods as well as the use of density gradients. Using these methods, microglial precursor cells are isolated and then transferred onto a solid support. Preferably, the microglial precursor cells are enriched by mechanical isolation based on morphology, such as for example described in the examples below.

In another preferred embodiment of the method of the disclosure, the medium in step (c) and/or the medium employed for growing the microglial precursor cells for the initial at least two passages further comprises up to 50 ng/ml M-CSF.

The term "M-CSF" as used herein refers to macrophage colony-stimulating factor, a secreted cytokine which influences hematopoietic stem cells to differentiate into macrophages or other related cell types (Takahashi et al., 1989). M-CSF may be comprised in the medium in amounts of up to 50 ng/ml, preferably between 1 to 40 ng/ml, more preferably between 3 and 30 ng/ml, such as for example 5 to 20 ng/ml, such as for example 7 to 15 ng/ml and most preferably at about 10 ng/ml.

In another preferred embodiment of the method of the disclosure, the medium in step (c) and/or the medium employed for growing the microglial precursor cells for the initial at least two passages further comprises up to 50 ng/ml IL-3.

The term "IL-3" as used herein refers to interleukin-3, an interleukin, that stimulates the differentiation of multipotent hematopoietic stem cells into myeloid progenitor cells as well as stimulating the proliferation of the cells of the myeloid lineage (erythrocytes, thrombocytes, granulocytes, monocytes, and dendritic cells) (Yang et al., 1986). IL-3 is secreted by activated T cells. IL-3 may be comprised in the medium in amounts of up to 50 ng/ml, preferably between 1 to 40 ng/ml, more preferably between 3 and 30 ng/ml, such as for example 5 to 20 ng/ml, such as for example 7 to 15 ng/ml and most preferably at about 10 ng/ml.

In a further preferred embodiment of the method of the disclosure, the medium in step (b) further comprises between 5 to 50 ng/ml laminin. Preferred amounts of laminin are as defined above.

In another preferred embodiment of the method of the disclosure, the concentration of FGF2 in the neural precursor selection medium in step (iii) is about 20 ng/ml and the amount of fibronectin is about 5 µg/ml.

In a further preferred embodiment of the method of the disclosure, the concentration of FGF2 in the medium in step (iv) is about 20 ng/ml and the amount of laminin is about 10 ng/ml.

In another preferred embodiment of the method of the disclosure, the medium in step (b) and/or the medium employed for growing the microglial precursor cells for the initial at least two passages comprises about 100 ng/ml GM-CSF, about 10 ng/ml M-CSF and about 10 ng/ml IL-3.

Any of the supplemental factors mentioned herein, e.g. insulin, insulin-like growth factor, GM-CSF, FGF2, fibronectin, laminin, poly-L-lysin, M-CSF and IL-3 may be obtained by methods well known in the art. Thus, they may for example be obtained by recombinant production or they may be obtained from natural sources. Furthermore, these factors may be present in the form of mixtures of factors, such as for example serum.

For recombinant production, for example, nucleic acid sequences encoding the above mentioned factors can be synthesized by PCR and inserted into an expression vector. Subsequently a suitable host may be transformed with the expression vector. Thereafter, the host is cultured to produce the desired factor, which is isolated and purified. Such methods are well known in the art (see, e.g., Sambrook et al., supra). An alternative method is in vitro translation of mRNA. Suitable cell-free expression systems include rabbit reticulocyte lysate, wheat germ extract, canine pancreatic microsomal membranes, *E. coli* S30 extract, and coupled transcription/translation systems such as the TNT-system (Promega).

In addition to recombinant production, the above mentioned factors may be produced synthetically, e.g. by direct protein synthesis using solid-phase techniques (cf. Stewart et al. (1969): Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. Furthermore, the above mentioned factors may also be produced semi-synthetically, for example by a combination of recombinant and synthetic production.

Preferably, the supplemental factors insulin, insulin-like growth factor, GM-CSF, FGF2, M-CSF and IL-3 are human proteins. More preferably, these factors are obtained by recombinant production.

In a further preferred embodiment of the method of the disclosure, the isolation of microglial precursor cells comprising CD45-positive cells in step (d) is performed by magnetic activated cell sorting (MACS) or flow cytometry activated cell sorting (FACS).

In another preferred embodiment of the method of the disclosure, the microglial precursor cells are characterised by the expression of CD45, CD11b, CD68, Iba1, integrin-alpha 4, inegrin-beta 1, CX3CR1 and TREM2.

All of these molecules characterising microglial precursor cells are defined in accordance with the present disclosure in the same manner as known in the prior art and the common general knowledge of the skilled person.

In accordance with the present disclosure, "CD11b" relates to cluster of differentiation 11b, a subunit of Mac-1, which is a complement receptor ("CR3") consisting of CD11b and CD18.

"CD68", in accordance with the present disclosure, relates to cluster of differentiation 68, a glycoprotein which binds to low density lipoprotein. It is expressed on monocytes/macrophages.

In accordance with the present disclosure, "Iba1" relates to ionized calcium binding adaptor molecule 1, a 17-kDa EF-hand protein that is specifically expressed in macrophages/microglia and is upregulated during the activation of these cells. Among brain cells, the Iba1 gene is specifically expressed in microglia. Upon activation of microglia due to inflammation, expression of Iba1 is upregulated allowing the detection of activated microglia.

The term "integrin-alpha 4", as used herein, refers to the α4 integrin subunit expressed on the cell membrane as a heterodimer non-covalently associated with the β1 or the β7 integrin chains. α4 integrins have a key function in the adhesion interaction between stem/progenitor cells and the stromal microenvironmental cells and their matrix within the bone marrow.

In accordance with the present disclosure, "integrin-beta 1", also known as ITGB1 or CD29, is an integrin unit associated with very late antigen receptors.

The term "CX3CR1" as used herein, refers to the only member of the CX3C sub-family of chemokine receptors. This receptor binds the chemokine CX3CL1 (described above), which is also known as neurotactin or fractalkine. Expression of this receptor is mainly associated with macrophages and monocytes (Jung et al., 2000).

"TREM2", in accordance with the present disclosure, refers to the triggering receptor expressed on myeloid cells 2, and is believed to have a role in chronic inflammation and the stimulation of production of constitutive rather than inflammatory chemokines and cytokines (Schmid et al., 2002; Takahashi et al., 2005). TREM2 forms a receptor signaling complex with TYROBP and triggers activation of the immune responses in macrophages and dendritic cells.

In a further preferred embodiment of the method of the disclosure, the microglial precursor cells are further characterized by an at least 2 fold increased expression of the gene transcripts for TNF-alpha, IL-1 beta, nitric oxide synthase-2, CCL2, CXCL9 and/or CXCL10 after stimulation with LPS as compared to cells not stimulated with LPS.

Also these inducible molecules characterizing microglial precursor cells are defined in accordance with the present disclosure in the same manner as known in the prior art and the common general knowledge of the skilled person.

"TNF-alpha", in accordance with the present disclosure, refers to tumor necrosis factor alpha, which is a cytokine involved in systemic inflammation and is a member of a group of cytokines that stimulate the acute phase reaction. TNF-alpha primarily regulates immune cells, but is also able to induce apoptotic cell death, to induce inflammation, and to inhibit tumorigenesis and viral replication. Dysregulation and, in particular, overproduction of TNF-alpha have been implicated in a variety of human diseases, as well as cancer. TNF-alpha is produced mainly by macrophages, but also by a broad variety of other cell types including lymphoid cells, mast cells, endothelial cells, cardiac myocytes, adipose tissue, fibroblasts, and neuronal tissue. Large amounts of TNF-alpha are released in response to lipopolysaccharide, other bacterial products, and IL-1 (interleukin-1).

In accordance with the present disclosure, "IL-1 beta" refers to a cytokine and is a member of the interleukin-1 cytokine family. IL-1 beta is produced by activated macrophages as a proprotein, which is proteolytically processed to its active form by caspase-1 (CASP1/ICE). IL-1 beta is an important mediator of the inflammatory response, and is involved in a variety of cellular activities, including cell proliferation, differentiation, and apoptosis.

As used herein, "nitric oxide synthase-2" belongs to a family of enzymes that carry out a 5'-electron oxidation of L-arginine with the aid of tetrahydro-biopterin. Nitric oxide synthase (NOS) enzymes contribute to the transmission between neurons, to the immune system and to dilating blood vessels. They do so by synthesis of nitric oxide (NO) from the terminal nitrogen atom of L-arginine in the presence of NADPH and dioxygen ($O_2$). Induction of the nitric oxide synthase-2 usually occurs in an oxidative environment, and thus high levels of nitric oxide have the opportunity to react with superoxide leading to peroxynitrite formation and cell toxicity. These properties are believed to define the roles of nitric oxide synthase-2 in host immunity, enabling its participation in anti-microbial and anti-tumor activities as part of the oxidative burst of macrophages.

In accordance with the present disclosure, "CCL2" refers to the chemokine (C-C motif) ligand 2. CCL2 is a small cytokine belonging to the CC chemokine family that is also known as monocyte chemotactic protein-1 (MCP-1). CCL2 recruits monocytes, memory T cells, and dendritic cells to sites of tissue injury and infection. Cell surface receptors that bind CCL2 are CCR2 and CCR4.

"CXCL9", as used throughout the present disclosure, refers to chemokine (C-X-C motif) ligand 9. CXCL9 is a small cytokine belonging to the CXC chemokine family that is also known as monokine induced by gamma interferon (MIG). CXCL9 is a T-cell chemo-attractant, which is induced by IFN-γ. CXCL9 elicits its chemotactic functions by interacting with the chemokine receptor CXCR3.

In accordance with the present disclosure, "CXCL10" refers to chemokine (C-X-C motif) ligand 10. CXCL10 is a small cytokine belonging to the CXC chemokine family that is also known as 10 kDa interferon-gamma-induced protein (γ-IP10 or IP-10). CXCL10 is secreted by several cell types in response to IFN-γ. These cell types include monocytes, endothelial cells and fibroblasts. CXCL10 has been attributed several roles, such as chemo-attraction for monocytes/macrophages, T cells, NK cells, and dendritic cells, promotion of T cell adhesion to endothelial cells, antitumor activity, and inhibition of bone marrow colony formation and angiogenesis. This chemokine elicits its effects by binding to the cell surface chemokine receptor CXCR3.

It has been shown that microglial precursor cells can be induced by pro-inflammatory cytokines of the bacterial toxin LPS to express the above mentioned factors (Napoli, 2008; Carter et al., 2007; Hughes et al., 2002; Gourmala et al., 1997). Thus, microglial precursor cells are characterised by an at least 2-fold increased expression of the gene transcripts for TNF-alpha, IL-1 beta, nitric oxide synthase-2, CCL2, CXCL9 and/or CXCL10 after stimulation with LPS as compared to cells not stimulated with LPS.

In another preferred embodiment of the method of the disclosure, the cells obtained are free of pathogens. Such pathogens are well known to the skilled person and include, without being limiting, viruses such as for example Hepatitis virus A, B, C, Epstein-Barr-Virus or HIV-Virus and bacteria such as for example mycoplasm or chlamydia.

Unless otherwise defined, all technical and scientific terms used herein have the same meaning as commonly understood by one of ordinary skill in the art to which this disclosure belongs. In case of conflict, the patent specification, including definitions, will prevail.

BRIEF DESCRIPTION OF THE DRAWINGS

The file of this patent contains at least one drawing/photograph executed in color. Copies of this patent with color drawing(s)/photograph(s) will be provided by the Office upon request and payment of the necessary fee.

The figures show.

DETAILED DESCRIPTION OF THE PREFERRED EMBODIMENT

The examples illustrate the disclosure:

EXAMPLE 1

Figure 1:
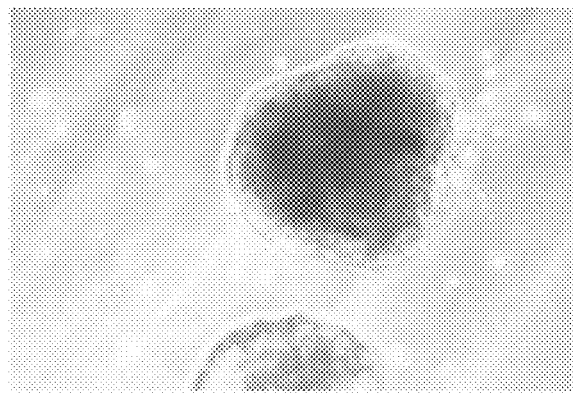
FIG. 1. Undifferentiated iPS spontaneously differentiate into embryoid bodies (EBs) (day 8 of EB formation).
Figure 2:
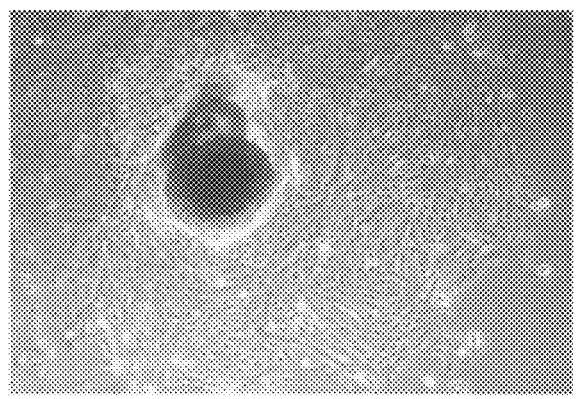
FIG. 2. Outgrowth of plated EBs in the selection stage (day 4) in B27-medium.
Figure 3:
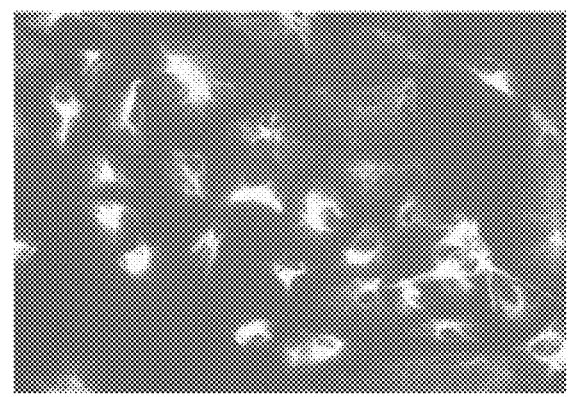
FIG. 3. Selection of nestin-positive cells 4 days in B27-medium.

Differentiation of Human Induced Pluripotent Stem Cells to Microglial Precursors For maintenance and expansion of human IFS, cells were cultured in chemically defined medium in the presence of 25 ng/ml recombinant human fibroblast growth factor-2 (rhFGF2) on a feeder layer. The absence of rhFGF2 and of self-renewal signals produced by feeder leads to spontaneous differentiation into embryoid bodies (EBs). EBs were kept in suspension for 8 days for spontaneous differentiation (FIG. 1). Then, they were plated on poly-L-ornithin (PLO) and fibronectin-coated dishes and neural precursors were selected for 14 days in B27-medium (Gibco/BRL/Invitrogen) supplemented with 20 ng/ml rhFGF2 and 5 μg/ml fibronectin or 10 ng/ml laminin to enhance cell survival (FIG. 2). In the selection stage, cells started to grow out and nestin-positive cells were the major population of developing cells (FIG. 3). During expansion of nestin-positive cells in N2-medium (Gibco/BRL/Invitrogen) supplemented with 20 ng/ml rhFGF2 and 10 ng/ml laminin, the number of cells increased. Differentiation was initiated by withdrawal of the growth factors after 10 days of expansion. After 2 weeks, different cell types had developed and were characterized for their cell identity by immunocytochemistry. Immunocytochemistry for βIII-tubulin after 14 days of differentiation showed developing clusters of βIII-tubulin-positive cells.

Figure 4:
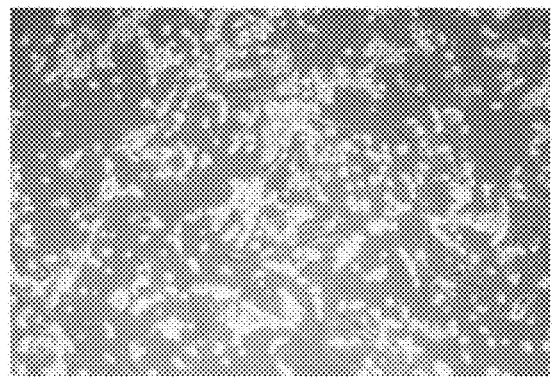
FIG. 4. Developing microglial-like colonies in culture after addition of the growth factors GM-CSF, IL-3 and M-CSF.

After 6 weeks of differentiation, cultures were immunolabeled for βIII-tubulin, glial fibrillary acidic protein (GFAP), CD45 and CD68 to identify the developing cell types. GFAP-positive as well as βIII-tubulin-positive cells were detected within the cultures indicating a differentiation of the neural precursors to astrocytes and neurons, respectively. Co-immunolabeling for GFAP and βIII-tubulin shows no co-expression with CD45, indicating that the CD45-positive cell population is distinct from astrocytes and neurons. To enhance development of microglial precursors cells 100 ng/ml recombinant human granulocytemacrophage colony-stimulating factor (rhGM-CSF), 10 ng/ml recombinant human interleukin-3 (rhIL-3) and 10 ng/ml recombinant human macrophage colony-stimulating factor (rhM-CSF) were added to the media. After 2 days, first microglial precursors appeared in the culture (FIG. 4) identified by immunostaining with antibodies directed against the hematopoietic marker protein CD45. After several days, approximately 2-10% of cells showed immunoreactivity for CD45. Cell colonies developed and microglial precursor lines proliferated in clusters within the mixed neural cultures.

EXAMPLE 2

Selection and Generation of Microglial Precursor Lines

Figure 5:
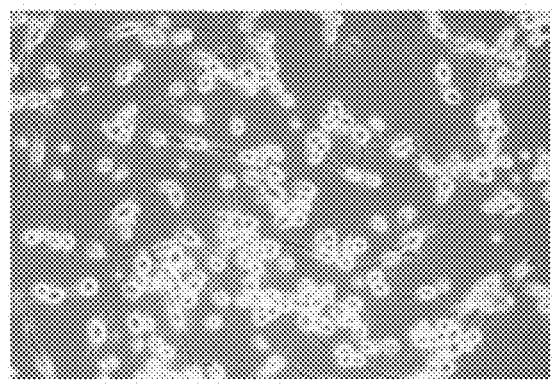
FIG. 5. Isolated microglial precursor lines after 6 weeks of differentiation on PLL-coated dishes in N2-medium supplemented with GM-CSF, IL-3 and M-CSF.
Figure 6:
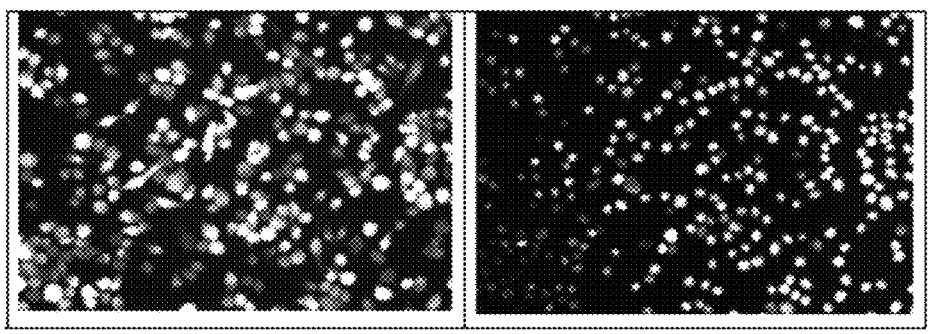
FIG. 6. Antibody against CD68 (left, DAPI right) immunostained about 98% of the isolated microglial precursors.
Figure 7:
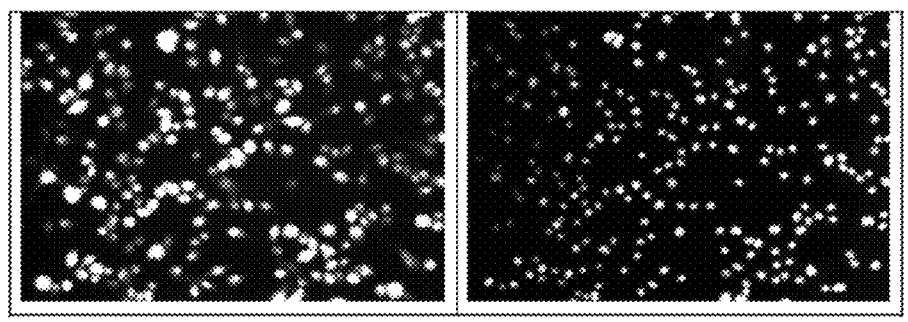
FIG. 7. Antibody against Iba1 (left, DAPI right) immunostained about 98% of the isolated microglial precursors.

For isolation of microglial precursor cells from the differentiated mixed culture a specific method was applied. Microglia-like cells identified by morphology were mechanically isolated by a micropipette and expanded on poly-L-lysine (PLL)-coated (5 μg/ml) dishes with the highest density possible for a monolayer. Mechanically isolated microglial precursors were cultured in the presence of 100 ng/ml rhGM-CSF, 10 ng/ml rhIL-3 and 10 ng/ml rhM-CSF. Growth factors are required for survival and proliferation of mechanically isolated microglial precursors. After expansion, cells expressing CD45 were sorted by magnetic activated cell sorting (MACS) or flow cytometry activated cell sorting (FACS) with antibodies directed against CD45. Sorted cells were cultured on PLL-coated dishes in N2 medium supplemented with 100 ng/ml rhGM-CSF, 10 ng/ml rhIL-3 and 10 ng/ml rhMCSF. After several days in culture, microglial precursor cell lines started to proliferate (FIG. 5). The phenotype of the cells differed from ramified over bipolar structured till completely rounded cell morphology. Cells were isolated by trypsin or cell scraper and split 1:3 till 1:5 twice a week. Cell identity of microglial precursor lines was verified by immunocytochemistry for CD68 and Iba1 (FIGS. 6 and 7).

EXAMPLE 3

Subcloning, Expansion and Quality Control of Microglial Precursor Lines

To obtain clones, single cells were mechanically isolated and transferred into separate PLL-coated (5 μg/ml) culture dishes. The isolated microglial precursor cells were cultured in DMEM/F12-medium (Gibco/BRL/Invitrogen) containing 100 ng/ml rhGM-CSF, 10 ng/ml rhIL-3 and 10 ng/ml rhM-CSF. Cells were cultured with high density and split 1:2. After splitting, cells recovered and attached again to the new PLL-coated dishes. Microglial precursors proliferated without addition of growth factors to medium after some passages and were passaged 1:3 till 1:5 twice a week. Microglial precursor cells were expanded to obtain at least $1 \times 10^{10}$ cells. Cells were analyzed by flow cytometry for expression of CD45, CD11b, CD11c, CD14, CD16, integrin-alpha4, integrin-beta1, CX3CR1 and TREM2. In addition, gene transcripts for TNF-alpha, interleukin-1 beta, nitric oxide synthase-2, CX3CL1, CCL2, CXCL9 and CXCL10 can be analyzed in the cells under normal and LPS-stimulation by real-time RT-PCR. The cells are confirmed by various test systems to be free of pathogens or contaminants (e.g. viruses etc.). Cells were aliquoted and frozen.

EXAMPLE 4

Figure 8:
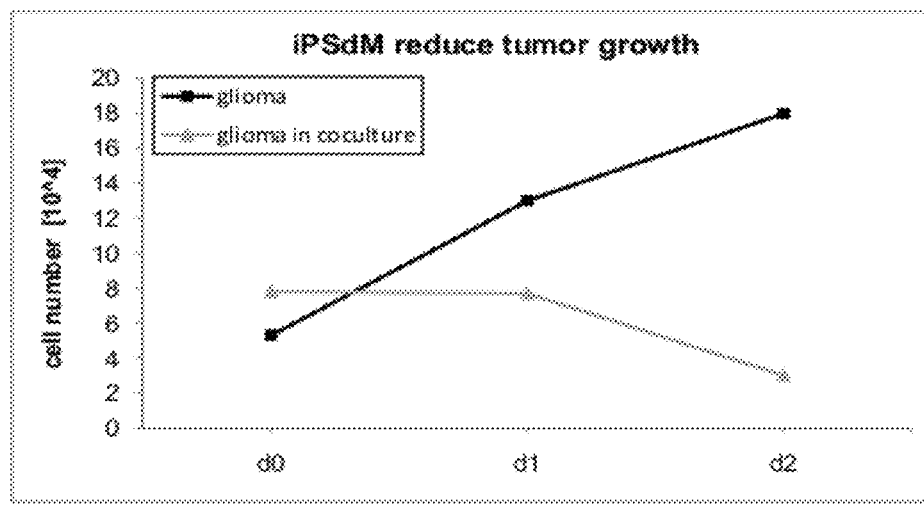
FIG. 8. Coculture of GFP-transduced human microglia derived from induced pluripotent stem cells (iPSdM) and the glioma cell line U87. Cell number per culture dish of U87 glioma cells was determined under fluorescence microscope on day 0 (d0), day 1 (d1) and day 2 (d2) after coculture or culture of U87 alone. Microglial cells (iPSdM) reduced glioma cell number over time.

In Vitro Experiments with Human Induced Pluripotent Stem Cell Derived Microglia and Glioma In vitro experiments were performed to confirm the functional activity of human iPS-derived microglia using the example of tumor growth. A co-culture of human GFP-transduced iPSdM and the human glioma cell line U87 was carried out using a ratio of 1:1 in co-culture. Starting the co-culture at day 0, every day total cell number of co-culture as well as the cell number of glioma in culture alone was counted under the microscope. Furthermore, the percentage of glioma and iPSdM in co-culture was measured by flow cytometry and the amount of glioma cells in the co-culture system was calculated (FIG. 8). Thus, a reduced amount of glioma cells was detected in the co-culture compared to the culture of glioma cells alone and suggest that glioma cells were phagocytosed by iPSdM. Thus, the iPS-derived migroglia precursors of the present disclosure are functionally active.

Next, it was analysed whether glioma were phagocytosed by microglia using flow cytometry. Glioma cells were labeled with the red membrane dye PKH26 and iPSdM were visualized by lentiviral transduction with GFP. Both cell types were co-cultured at a ratio of 1:1. As control labeled glioma and GFP-transduced iPSdM were cultivated alone. After two days cells were analyzed by flow cytometry showing that about 97% of the green cells were also positive for a red fluorescent dye. This indicates that almost all iPSdM started to phagocyte red labeled glioma cells (data not shown).

REFERENCES

Banati, R. B. (2003). Neuropathological imaging: in vivo detection of glial activation as a measure of disease and adaptive change in the brain. Br Med Bull 65, 121-131.

Biber, K., Neumann, H., Inoue, K., and Boddeke, H. W. (2007). Neuronal 'On' and 'Off' signals control microglia. Trends Neurosci 30, 596-602.

Blasi, E., Barluzzi, R., Bocchini, V., Mazzolla, R., and Bistoni, F. (1990). Immortalization of murine microglial cells by a v-raf/v-myc carrying retrovirus. J Neuroimmunol 27, 229-237.

Block, M. L., and Hong, J. S. (2007). Chronic microglial activation and progressive dopaminergic neurotoxicity. Biochem Soc Trans 35, 1127-1132.

Bocchini, V., Mazzolla, R., Barluzzi, R., Blasi, E., Sick, P., and Kettenmann, H. (1992). An immortalized cell line expresses properties of activated microglial cells. J Neurosci Res 31, 616-621.

Carter S L, Müller M, Manders P M, Campbell I L. (2007). Induction of the genes for Cxcl9 and Cxcl10 is dependent on IFN-gamma but shows differential cellular expression in experimental autoimmune encephalomyelitis and by astrocytes and microglia in vitro. Glia. 55(16):1728-39.

Chan, W. Y., Kohsaka, S., and Rezaie, P. (2007). The origin and cell lineage of microglia: new concepts. Brain Res Rev 53, 344-354.

Choi, K. D., Yu, J., Smuga-Otto, K., Salvagiotto, G., Rehrauer, W., Vodyanik, M., Thomson, J., and Slukvin, I. (2009). Hematopoietic and endothelial differentiation of human induced pluripotent stem cells. Stem Cells 27, 559-567.

Dainiak M B, Kumar A, Galaev I Y, Mattiasson B. (2007). Methods in cell separations. Adv Biochem Eng Biotechnol. 2007; 106:1-18.

Durkin, M. E., Loechel, F., Mattei, M. G., Gilpin, B. J., Albrechtsen, R. and Wewer, U. M. (1997). Tissue-specific expression of the human laminin alpha5-chain, and mapping of the gene to human chromosome 20q13.2-13.3 and to distal mouse chromosome 2 near the locus for the ragged (Ra) mutation. FEBS Lett. 411 (2-3), 296-300.

Ford A L, Goodsall A L, Hickey W F, Sedgwick J D. (1995). Normal adult ramified microglia separated from other central nervous system macrophages by flow cytometric sorting. Phenotypic differences defined and direct ex vivo antigen presentation to myelin basic protein-reactive CD4+ T cells compared. J Immunol. 154(9):4309-21.

Giulian, D., and Baker, T. J. (1986). Characterization of ameboid microglia isolated from developing mammalian brain. J Neurosci 6, 2163-2178.

Gourmala N G, Buttini M, Limonta S, Sauter A, Boddeke H W. (1997). Differential and time-dependent expression of monocyte chemoattractant protein-1 mRNA by astrocytes and macrophages in rat brain: effects of ischemia and peripheral lipopolysaccharide administration. J Neuroimmunol. 74(1-2):35-44.

Hanisch, U. K., and Kettenmann, H. (2007). Microglia: active sensor and versatile effector cells in the normal and pathologic brain. Nat Neurosci 10, 1387-1394.

Horvath, R. J., Nutile-McMenemy, N., Alkaitis, M. S., and Deleo, J. A. (2008). Differential migration, LPS-induced cytokine, chemokine, and NO expression in immortalized BV-2 and HAPI cell lines and primary microglial cultures. J Neurochem 107, 557-569.

Hughes P M, Botham M S, Frentzel S, Mir A, Perry V H. (2002). Expression of fractalkine (CX3CL1) and its receptor, CX3CR1, during acute and chronic inflammation in the rodent CNS. Glia. 37(4):314-27.

Iwasaki, H., Somoza, C., Shigematsu, H., Duprez, E. A., Iwasaki-Arai, J., Mizuno, S., Arinobu, Y., Geary, K., Zhang, P., Dayaram, T., Fenyus, M. L., Elf, S., Chan, S., Kastner, P., Huettner, C. S., Murray, R., Tenen, D. G. and Akashi, K. (2005). Distinctive and indispensable roles of PU.1 in maintenance of hematopoietic stem cells and their differentiation. Blood 106(5): 1590-1600.

Jung S, Aliberti J, Graemmel P, Sunshine M J, Kreutzberg G W, Sher A, Littman D R. (2000). Analysis of fractalkine receptor CX(3)CR1 function by targeted deletion and green fluorescent protein reporter gene insertion. Mol Cell Biol. 20(11):4106-14.

Kamihira M, Kumar A. (2007). Development of separation technique for stem cells. Adv Biochem Eng Biotechnol. 2007; 106:173-93.

Klimanskaya, I., Chung, Y., Becker, S., Lu, S. J., Lanza, R. (2006). Human embryonic stem cell lines derived from single blastomeres. Nature 444(7118):481-5.

Kurokawa, T., Sasada, R., Iwane, M. and Igarashi, K. (1987). Cloning and expression of cDNA encoding human basic fibroblast growth factor FEBS Lett. 213 (1), 189-194.

Lafortune L, Nalbantoglu J, Antel J P. (1996). Expression of tumor necrosis factor alpha (TNF alpha) and interleukin 6 (IL-6) mRNA in adult human astrocytes: comparison with adult microglia and fetal astrocytes. J Neuropathol Exp Neurol. 55(5):515-21.

Lee F., Yokota, T., Otsuka, T., Gemmell, L., Larson, N., Luh, J., Arai, K. and Rennick, D. (1985). Isolation of cDNA for a human granulocyte-macrophage colony-stimulating factor by functional expression in mammalian cells Proc. Natl. Acad. Sci. U.S.A. 82 (13), 4360-4364.

Liu W, Brosnan C F, Dickson D W, Lee S C. (1994). Macrophage colony-stimulating factor mediates astrocyte-induced microglial ramification in human fetal central nervous system culture. Am J Pathol. 145(1):48-53.

Napoli, I. (2008). Establishment of Embryonic Stem Cell Derived Microglial Precursors and Application in an Animal Model of Alzheimer's Disease; PhD. thesis at the Faculty of Mathematics and Natural Sciences of the Rheinische Friedrich-Whilhelms University of Bonn.

Napoli, I., Kierdorf, K., and Neumann, H. (2009). Microglial precursors derived from mouse embryonic stem cells. Glia.

Nimmerjahn, A., Kirchhoff, F., and Helmchen, F. (2005). Resting microglial cells are highly dynamic surveillants of brain parenchyma in vivo. Science 308, 1314-1318.

Nishikawa S, Goldstein R A, Nierras C R. (2008) The promise of human induced pluripotent stem cells for research and therapy. Nat Rev Mol Cell Biol 9(9):725-9.

Park, I. H., and Daley, G. Q. (2009). Human iPS cell derivation/reprogramming. Curr Protoc Stem Cell Biol Chapter 4, Unit 4A 1.

Park, I. H., Lerou, P. H., Zhao, R., Huo, H., and Daley, G. Q. (2008). Generation of human-induced pluripotent stem cells. Nat Protoc 3, 1180-1186.

Pevny L H, Sockanathan S, Placzek M, Lovell-Badge R. (1998). A role for SOX1 in neural determination. Development 125(10):1967-78).

Ransohoff, R. M. and Perry, V. H. (2009). Microglial physiology: unique stimuli, specialized responses. Annu Rev Immunol. 27:119-45.

Ruegg, C., Postigo, A. A., Sikorski, E. E., Butcher, E. C., Pytela, R. and Erle, D. J. (1992). Role of integrin alpha 4 beta 7/alpha 4 beta P in lymphocyte adherence to fibronectin and VCAM-1 and in homotypic cell clustering. J. Cell Biol. 117 (1), 179-189.

Schmid C D, Sautkulis L N, Danielson P E, Cooper J, Hasel K W, Hilbush B S, Sutcliffe J G, Carson M J. (2002). Heterogeneous expression of the triggering receptor expressed on myeloid cells-2 on adult murine microglia. J Neurochem. 83(6):1309-20.

Schmitz, S. (2009). Der Experimentator: Zellkultur. Spektrum Akademischer Verlag, 2. Aufl.

Takahashi, M., Hirato, T., Takano, M., Nishida, T., Nagamura, K., Kamogashira, T., Nakai, S. and Hirai, Y. (1989). Amino-terminal region of human macrophage colony-stimulating factor (M-CSF) is sufficient for its in vitro biological activity: molecular cloning and expression of carboxyl-terminal deletion mutants of human M-CSF. Biochem. Biophys. Res. Commun. 161 (2), 892-901

Takahashi K, Rochford C D, Neumann H. (2005). Clearance of apoptotic neurons without inflammation by microglial triggering receptor expressed on myeloid cells-2. J Exp Med. 201(4):647-57.

Takashima Y, Era T, Nakao K, Kondo S, Kasuga M, Smith A G, Nishikawa S. (2007). Neuroepithelial cells supply an initial transient wave of MSC differentiation. Cell 129(7): 1377-88.

Tsuchiya, T., Park, K. C., Toyonaga, S., Yamada, S. M., Nakabayashi, H., Nakai, E., Ikawa, N., Furuya, M., Tominaga, A., and Shimizu, K. (2005). Characterization of microglia induced from mouse embryonic stem cells and their migration into the brain parenchyma. J Neuroimmunol 160, 210-218.

Vaughan, D. W., and Peters, A. (1974). Neuroglial cells in the cerebral cortex of rats from young adulthood to old age: an electron microscope study. J Neurocytol 3, 405-429.

Vuolteenaho, R., Chow, L. T. and Tryggvason, K. (1990). Structure of the human laminin B1 chain gene. J. Biol. Chem. 265 (26), 15611-15616.

Wong, G. G., Witek, J. S., Temple, P. A., Wilkens, K. M., Leary, A. C., Luxenberg, D. P., Jones, S. S., Brown, E. L., Kay, R. M., Orr, E. C., Shoemaker, C., Golde, D. W., Kaufman, R. J., Hewick, R. M., Wang, E. A. and Clark, S. C. (1985). Human GM-CSF: molecular cloning of the complementary DNA and purification of the natural and recombinant proteins. Science 228 (4701), 810-815.

Yang, Y. C., Ciarletta, A. B., Temple, P. A., Chung, M. P., Kovacic, S., Witek-Giannotti, J. S., Leary, A. C., Kriz, R., Donahue, R. E., Wong, G. G. et al. (1986). Human IL-3 (multi-CSF): identification by expression cloning of a novel hematopoietic growth factor related to murine IL-3. Cell 47 (1), 3-10.

Zhang, J., Wilson, G. F., Soerens, A. G., Koonce, C. H., Yu, J., Palecek, S. P., Thomson, J. A., and Kamp, T. J. (2009). Functional cardiomyocytes derived from human induced pluripotent stem cells. Circ Res 104, e30-41.

Zhou W, Freed C R. (2009). Adenoviral gene delivery can reprogram human fibroblasts to induced pluripotent stem cells. Stem Cells 27(11):2667-74.

What is claimed is:

1. A method for obtaining human microglial precursor cells, comprising:
    (a) providing a cell population comprising neural precursor cells, wherein the cell population is obtainable from embryoid bodies differentiated from human pluripotent stem cells;
    (b) differentiating the cell population comprising neural precursor cells into microglial precursor cells by culturing in a medium comprising 5 to 500 µg/ml insulin, 100 ng/ml GM-CSF, 10 ng/ml IL-3 and 10 ng/ml M-CSF in the absence of FGF2,
    (c) expanding and enriching microglial precursor cells in a medium comprising 25 µg/ml insulin and 100 ng/ml GM-CSF; and
    (d) isolating microglial precursor cells positive for CD45.

2. The method of claim 1, wherein the cell population comprising neural precursor cells in step (a) is obtained by:
    (i) growing human pluripotent stem cells in suspension culture until embryoid bodies have formed;
    (ii) transferring the embryoid bodies onto a solid support under conditions suitable to allow attachment of the embryoid bodies and culturing the embryoid bodies until the embryoid bodies have attached to the solid support;
    (iii) changing the medium to a neural precursor selection medium for enrichment of nestin-positive cells comprising
        (1) a growth factor selected from the group consisting of: insulin and insulin-like growth factors;
        (2) 5 to 100 ng/ml FGF2; and
        (3) 2.5 to 25 µg/ml fibronectin or 5 to 50 ng/ml laminin and culturing the embryoid bodies for at least 10 days; and
    (iv) expanding nestin-positive cells in a medium comprising a growth factor selected from the group consisting of: insulin, insulin-like growth factors, 5 to 100 ng/ml FGF2, and 5 to 50 ng/ml laminin for at least 7 days.

3. The method of claim 1, wherein the cells are further cultured after step (d) for at least 2 passages in a medium comprising a growth factor selected from the group consisting of: insulin, insulin-like growth factors, and 10 to 150 ng/ml GM-CSF on a solid support under conditions suitable to allow attachment of the cells.

4. The method of claim 3, wherein following the culturing for 2 passages the microglial precursor cells are maintained in a medium comprising a growth factor selected from the group consisting of: insulin and insulin-like growth factors.

5. The method of claim 1, wherein enriching in step (c) comprises transferring microglial precursor cells onto a solid support under conditions suitable to allow attachment of the cells.

6. The method of claim 1, wherein the medium in step (c) of claim 1 further comprises up to 50 ng/ml M-CSF.

7. The method of claim 1, wherein the medium in step (b) of claim 1 further comprises between 5 to 50 ng/ml laminin.

8. The method of claim 2, wherein the concentration of FGF2 in the neural precursor selection medium in step (iii) is 20 ng/ml and the amount of fibronectin is 5 µg/ml.

9. The method of claim 2, wherein the concentration of FGF2 in the medium in step (iv) is 20 ng/ml and the amount of laminin is 10 ng/ml.

10. The method of claim 1, wherein the isolation of microglial precursor cells comprising CD45-positive cells in step (d) is performed by magnetic activated cell sorting (MACS) or flow cytometry activated cell sorting (FACS).

11. The method of claim 1, wherein the microglial precursor cells are characterized by the expression of CD45, CD11b, CD68, Iba1, integrin-alpha4, inegrin-beta1, CX3CR1 and TREM2.

12. The method of claim 1, wherein the microglial precursor cells are further characterized by an at least 2 fold increased expression of the gene transcripts for TNF-alpha, interleukin-1beta, nitric oxide synthase-2, CX3CL1, CCL2, CXCL9 and/or CXCL10 after stimulation with LPS as compared to cells not stimulated with LPS.

13. The method of claim 1, wherein the cells obtained are free of pathogens.

* * * * *